United States Patent [19]

Albert

[11] Patent Number: 4,519,092
[45] Date of Patent: May 21, 1985

[54] SCANNING X-RAY SPECTROMETRY METHOD AND APPARATUS

[76] Inventor: Richard D. Albert, 317 Hartford Rd., Danville, Calif. 94526

[21] Appl. No.: 437,037

[22] Filed: Oct. 27, 1982

[51] Int. Cl.³ ............... G01N 21/24; G01N 23/20
[52] U.S. Cl. ................................. 378/045; 378/100
[58] Field of Search .............. 378/43, 44, 45, 99, 378/100, 147

[56] References Cited

U.S. PATENT DOCUMENTS

| | | | |
|---|---|---|---|
| 2,730,566 | 1/1956 | Bartow et al. | 378/147 |
| 3,925,660 | 12/1975 | Albert | 250/272 |
| 3,949,229 | 4/1976 | Albert | 250/401 |
| 3,983,397 | 9/1976 | Albert | 250/406 |
| 4,032,787 | 6/1977 | Albert | 250/402 |
| 4,048,496 | 9/1977 | Albert | 250/272 |
| 4,057,745 | 11/1977 | Albert | 378/99 |
| 4,104,519 | 8/1978 | Oldendorf | 378/44 |
| 4,144,457 | 3/1979 | Albert | 250/445 T |
| 4,149,076 | 4/1979 | Albert | 250/402 |
| 4,196,351 | 4/1980 | Albert | 250/416 TV |
| 4,259,582 | 3/1981 | Albert | 250/402 |
| 4,259,583 | 3/1981 | Albert | 250/416 TV |
| 4,288,697 | 9/1981 | Albert | 250/505 |
| 4,317,036 | 2/1982 | Wang | 378/45 |
| 4,439,680 | 3/1984 | Broadhurst | 250/310 |

OTHER PUBLICATIONS

Rolf Woldseth, X-Ray Spectrometry, Chapter 4, pp. 4.1 to 4.17, Published 1973 by Kevex Corp., Foster City, California.

Brochure entitled Model 6110-60 Specifications-TEFA X-Probe Published by EG&G ORTEC, date and author not known.

Brochure entitled The PGT 800-Composition and Thickness Analyzer Published by Princeton Gamma-Tech, date and author not known.

Primary Examiner—Alfred E. Smith
Assistant Examiner—T. N. Grigsby
Attorney, Agent, or Firm—Phillips, Moore, Lempio & Finley

[57] ABSTRACT

The distribution of one or more chemical elements within an object is detected by directing primary x-rays to successive points along a scan path on the object and by analyzing the energies of fluorescent x-rays emitted from the successive points to identify characteristic x-rays of the element. In the preferred form, a moving primary x-ray origin point is established by sweeping an electron beam along a broad target plate in a raster pattern corresponding to the desired scan path on the object. A collimator between the target plate and the object has x-ray transmissive zones alternated with x-ray absorbent zones to assure that primary x-rays from the moving origin point reach only corresponding successive points on the object. High precision with a minimum of structural complication is realized by scanning electronically rather than with a mechanical system.

10 Claims, 3 Drawing Figures

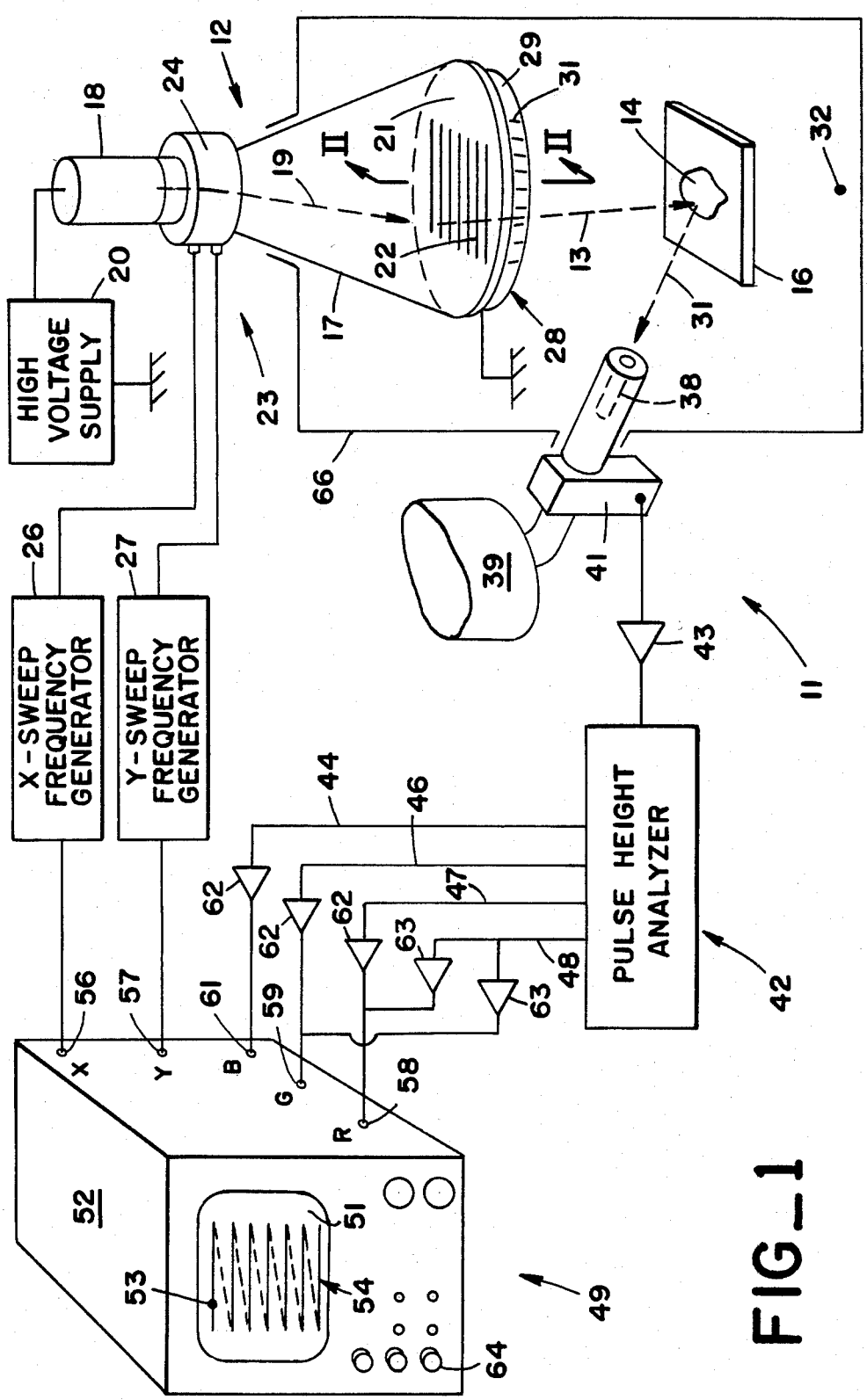
FIG_1

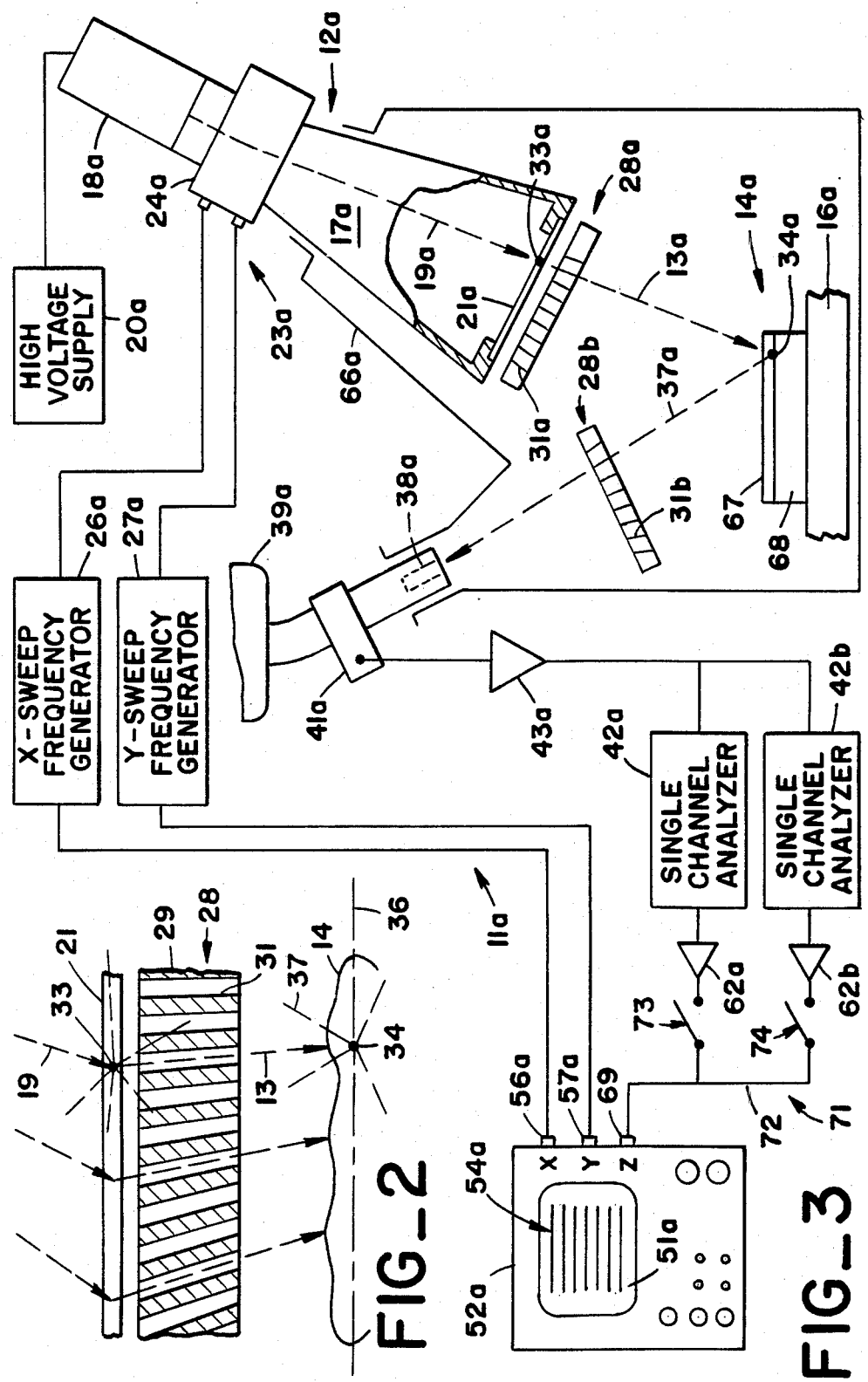

SCANNING X-RAY SPECTROMETRY METHOD AND APPARATUS

TECHNICAL FIELD

This invention relates to the detection of the spatial distribution of one or more chemical elements within an object or region. More particularly the invention relates to methods and apparatus in which elements are detected by analyzing the energies of fluorescent X-rays which are emitted from the region of interest in response to scanning of the region with a primary radiation.

BACKGROUND OF THE INVENTION

Irradiation of most substances results in the emission of secondary or fluorescent x-rays having wavelengths or energies that are determined by the kinds of chemical elements that are present in the substance. Each element fluoreses x-rays having a different energy or combination of energies which are known as the characteristic x-rays of the element. Consequently it is possible to detect the presence and amounts of particular elements in a substance by irradiating the substance and then analyzing the energies of the resulting fluorescent x-rays.

In some cases it is desirable not only to detect the presence of one or more elements but also to determine the spatial distribution of such elements within an object or region.

In the quality control of manufactured products, such as printed circuits for example, it may be desirable to check the uniformity of metallic plating on a base material. Detection of variations in the concentration of an element within an object may also be highly useful in the analysis of ore samples. Considering still another example, certain elements tend to concentrate in certain specific regions of the human body. Iodine, for example, concentrates in the thyroid gland and it can be useful for medical diagnostic purposes to obtain an image showing variations in the distribution of the iodine within the gland. Information about the distribution of chemical elements in objects, samples and specimens of various kinds is also useful for a variety of other purposes.

To detect the distribution of one or more elements within an object by x-ray fluorescence analysis, the primary radiation is directed to only a localized small area of the object at any given time. The small irradiation area is traveled along a scan path on the object and x-ray fluorescence emitted from successive points along the scan path is detected and analyzed to identify x-rays having energies characteristic of the element or elements of interest. A uniform count of characteristic x-rays during the scanning operation indicates a uniform distribution of the corresponding element. Variations in the rate of detection of the characteristic x-rays during the scan indicate corresponding variations in the concentration of the element within the scanned region.

A visible display of the distribution of the element may be produced by synchronizing the raster control of a cathode ray tube or the like with the scanning motion at the object while modulating the intensity control of the tube in accordance with the characteristic x-ray detection rate. Where the display is to depict the distribution of more than one element, the characteristic x-ray count rate signal for each element may be used to modulate a different one of the color intensity controls of a cathode ray tube which presents multi-color displays. Alternately, the distribution data may be processed by a graphical printer or may be digitized and printed out in alphanumeric form.

Scanning x-ray spectrometers have been subject to serious problems and limitations that derive from the systems heretofore used to irradiate only a small area of the object which is being analyzed and to travel the area of irradiation along a scan path on the object.

In the first general type scanning x-ray spectrometer the primary radiation which excites x-ray fluorescence is an electron beam. The beam is swept along the scan path, typically through a raster pattern of parallel scan lines, by magnetic or electrostatic deflection means. As a practical matter, a scanning electron microscope structure is usually adapted to perform the scanning operation.

Electrons do not penetrate very far into the object which is being examined. Consequently only the distribution of an element near the surface can be detected. A further limitation is present in that the object must be an electrical conductor. If it is not a conductor, electrical charge builds up on the surface of the object and causes distortions in the operation of the system and in the output data. In some cases, non-conductors can be analyzed by applying a thin coating of metal such as gold to the object but at best this requires a substantial complication of sample preparation procedures. Direct scanning of an object with an electron beam requires that the object be disposed in a vacuum chamber. This complicates the structure and slows operation as evacuation of the chamber, prior to each examination of a specimen, requires a significant amount of time. The need to maintain a vacuum at the surface of the object being scanned generally prevents use of this kind of system for analysis of living tissue.

Each of the problems and limitations discussed above can be avoided by utilizing a second known type of scanning x-ray spectrometer in which the primary radiation source is an x-ray tube. X-rays generated by the tube are blocked from the object which is being examined except for those x-rays which travel along a single narrow collimator passage directed towards the object. A motor driven mechanical system moves the x-ray tube including the collimator in a predetermined pattern to accomplish the scanning operation.

Mechanical scanning is inherently very slow in comparison with electronic scanning. Exposure times are longer. Factors such as vibrations and positional imprecisions in moving mechanical parts detract from the accuracy of the information produced by the system. Efforts to minimize such factors require an extremely costly construction. Thus resolution of the problems discussed above with respect to electron beam scanning has heretofore been accomplished only by accepting the other equally serious problems and limitations inherent in mechanical scanning.

The present invention is directed to overcoming one or more of the problems set forth above.

SUMMARY OF THE INVENTION

In one aspect of the present invention an x-ray spectrometer for detecting the distribution of at least one chemical element within an object has scanning means for directing primary x-rays to successive points situated along a scan path on the object and means for detecting variations of the amount of the element along the scan path by analyzing the energy of fluorescent x-rays emitted from the object in response to the primary x-rays. The scanning means has a charged particle beam source, a target plate formed of material which produces x-rays in response to the charged particle beam and beam deflector means for sweeping the charged particle beam along an impact path on the plate which corresponds to the scan path on the object.

In another aspect, the invention further includes a collimator situated between the target plate and the scan path, the collimator having a volume of x-ray absorbent material transpierced by a plurality of radiation transmissive zones which are directed at the successive points along the scan path.

In still another aspect, the invention provides a method of determining the spatial distribution of at least one chemical element within a subject, in which primary x-rays are directed to a scan path at the subject, and in which the relative amounts of the chemical element at locations along the scan path are determined by analyzing the energies of fluorescent x-rays emitted from the locations in response to the primary x-rays. A moving origin point of the primary x-rays is generated by directing a charged particle beam to a relatively broad target and by deflecting the charged particle beam to travel the impact point of the beam on the target along an impact path which corresponds to the scan path at the subject.

In a further aspect of the invention the method includes the steps of sequentially transmitting the primary x-rays from the moving origin point to each of the locations along the scan path while blocking the primary x-rays from others of the locations.

Thus the invention employs penetrating x-rays as the primary radiation for initiating x-ray fluorescence in the scanned object while providing for the scanning motion by electronic techniques. This avoids the disadvantages of each of the prior art systems hereinbefore described while retaining the advantages of each. Scans can be accomplished very rapidly and with very high precision. The scanned object need not necessarily be situated in a vacuum and time consuming special preparation of specimens is not usually needed. Where the output data is to be presented in the form of a visual display, high resolution can be achieved and magnification or demagnification of the display image relative to the scanned region is easily provided for. The system is adaptable to the scanning of diverse types of subjects including living tissue.

The invention can be further understood by reference to the accompanying drawings and to the following description of specific examples.

BRIEF DESCRIPTION OF THE DRAWINGS

In the accompanying drawings:

FIG. 1 is a diagramatic view of a scanning x-ray spectrometer in accordance with one embodiment of the invention which embodiment is adapted to the general purpose analysis of any of a variety of different objects to determine the spatial distribution of one or more chemical elements within the object;

FIG. 2 is an enlarged cross section view taken along line II—II of FIG. 1 illustrating how a scanning action with x-rays may be accomplished electronically; and FIG. 3 is a diagrammatic view depicting a scanning x-ray spectrometer in accordance with a second embodiment of the invention which is particularly adapted for detecting variations in the thickness of a layer of material situated on a differing base material.

DETAILED DESCRIPTION OF PREFERRED EMBODIMENTS OF THE INVENTION

Referring initially to FIG. 1 of the drawings, a scanning x-ray spectrometer 11 in accordance with this embodiment of the invention includes a scanning x-ray source 12 positioned to direct primary x-rays 13 to the object or region 14 in which the spatial distribution of one or more chemical elements is to be analyzed. Means 16 for supporting the object 14 may in some cases be a simple platform as in this example but a variety of other supports, holders or containers may also be used depending on the configuration and other physical characteristics of the object, specimen or sample 14 which is to be examined.

Portions of the scanning x-ray source 12 resemble a cathode ray tube and thus include a vacuum envelope 17 having a cathode and electron gun 18 at one end which directs an electron beam 19 towards an anode or target plate 21 at the opposite end. Target plate 21 is electrically grounded in this example and a negative high voltage supply 20 is connected to the cathode and electron gun 18. Thus electrons in the electron beam 19 are accelerated in passage between the electron gun 18 and target plate 21. Similar electron beam acceleration may be achieved by grounding cathode and electron gun 18 while connecting target plate 21 to a positive high voltage supply.

Electron beam 19 is traveled along an impact path 22 on target plate 21, the impact path typically being a raster pattern of parallel scan lines although in some instances useful information may be obtained from a single line scan. The beam deflection means 23 for this purpose is a magnetic deflector yoke 24 encircling the neck of vacuum envelope 17 in this example but an electrostatic deflection system of known form may also be used. X and Y sweep frequency generators 26 and 27 respectively are connected to yoke 24 to establish the impact path 22 raster.

Scanning x-ray source 12 differs from a standard cathode ray tube in that supply 20 applies a sufficiently high negative voltage to electron gun 18 to cause the electron beam 19 to generate substantial amounts of primary x-rays 13 by impaction on target plate 21 and in that the target plate is formed at least in part of a material, such as tungsten as one example, which promotes such x-ray generation. In embodiments such as this example in which the object 14 to be scanned is situated at the opposite side of target plate 21 from electron beam 19, the target plate is made sufficiently thin to transmit a sizable proportion of the primary x-rays 13. A thicker target plate 21 may be used if the x-rays that are emitted from the inside surface of the plate are employed for scanning instead of the x-rays which are transmitted through the plate as in this example.

Referring now to FIG. 2 in conjunction with FIG. 1, a collimator 28 is situated between target plate 21 and object 14 preferably in close proximity to the target plate. The collimator 28 has a body 29 formed at least in part of radiation absorbant material such as lead for example and which is transpierced by an array of spaced apart radiation transmissive zones 31 each of which extends between a separate point on the target plate 21 and a corresponding separate point in the region of the object 14. The zones 31 may be open passages or may be defined by x-ray transmissive material.

For clarity of illustration the radiation transmissive zones 31 are depicted in the drawings as being fewer in number and of larger diameter and spacing than is usually preferable. Definition and resolution in the results of a scanning operation are enhanced by minimizing the diameter and spacing of the zones 31. This may be accomplished by employing a collimator of the type described in my prior U.S. Pat. No. 4,288,697 issued Sept. 8, 1981 and entitled LAMINATE RADIATION COLLIMATOR which discloses techniques for manufacturing a collimator with as many as one hundred transmissive zones per linear centimeter of collimator surface and in which the zones may have a diameter of less than 100 microns.

In this embodiment, the zones 31 of the collimator 28 are each directed towards a focal point 32 located beyond the object 14 and thus are convergent. A focussing collimator 28 of this kind enhances accuracy in situations where the region of the object 14 that is to be scanned is smaller than the electron beam raster pattern 22 at target plate 21. Where this is not the case, the zones 31 may be parallel or may be divergent as in another embodiment to be hereinafter described.

As shown in FIG. 2, the origin point 33 of the primary x-rays 13 is the point of impact of the electron beam 19 at target plate 21 and x-rays are emitted in all directions from the origin point. Collimator 28 absorbs the x-rays which are emitted in the direction of object 14 except for the particular x-rays 13 that are emitted along the adjacent one of the radiation transmissive zones 31 of the collimator. Thus an x-ray irradiation point 34 travels along a scan path 36 on the object 14 in synchronism with the moving x-ray origin point 33 at target plate 21.

The primary x-rays 13, produced by abrupt deceleration of high energy electrons, include a continuous spectrum of energies or wavelengths. Such x-rays cause secondary or fluorescent x-rays 37 to be emitted in all directions from the traveling irradiation area 34 at object 14. Unlike the primary x-rays 13, the fluorescent x-rays 37 have a specific energy or limited number of specific energies determined by the chemical element at which the x-ray or x-rays originate and which is different for each different element. Thus the element or elements at the irradiation area 34 at a particular time can be identified by detecting the energies of the fluorescent x-rays 37 which are emitted from the object 14 at that time.

Referring again to FIG. 1, means for detecting the fluorescent x-rays 37 may be a solid state detector 38 positioned to receive x-rays emitted by object 14. Additional detectors 38 may be provided in instances where that is desirable to increase the count rate. Detector 38 in this example is of the known form which is cooled by liquid nitrogen from a cryostat 39 and which has a preamplifier 41 that produces electrical pulses having amplitudes proportional to the energies of x-rays intercepted by the detector. High resolution solid state detectors that do not require cooling may also be used to detect x-rays 37 or other energy dispersive detectors, such as spark chambers, gas filled or liquid Xenon proportional counters or scintillator-photomultiplier detectors, may be employed.

Output pulses from preamplifier 41 are transmitted to a pulse height analyzer 42 by a linear amplifier 43 which suppresses circuit noise by amplitude discrimination and which shapes the pulses for pulse height analysis. Pulse height analyzer 42 may be of the known form having a series of output channels 44, 46, 47, 48 and in which incoming pulses having one of a series of predetermined different amplitude ranges produce an output count at an individual one of the output channels that identifies that amplitude range. Thus an incoming pulse having an amplitude indicating detection of a first chemical element results in a count at the first output channel 44 and amplitudes indicative of a second chemical element produce counts at the second output channel 46. A pulse height analyzer 42 having additional output channels may be used if it is desired to determine the spatial distribution of a larger number of chemical elements during a single scanning operation.

In order to display or otherwise represent the spatial distribution of a chemical element within the scanned region of object 14, element identifying output counts at the corresponding output channel 44, 46, 47 or 48 must be correlated with a location within the object. More particularly, the count must be correlated with the origin point of the fluorescent x-ray that initiated the count. The X and Y sweep frequency signals from generators 26 and 27 are utilized for this purpose. At any given instant the sweep frequency signals have a unique combination of amplitudes which identifies the momentary location of the small irradiated area 34 depicted in FIG. 2. Thus the sweep frequency signals are also, in effect, scan position signals. The sweep frequency signal amplitudes together with count signals which concurrently appear on one of the output channels 44, 46, 47, 48 of the pulse height analyzer 42 may, for example, be digitized for print out by a data processor in alphanumeric form.

This embodiment of the invention employs a different means 49 for correlating the pulse height analyzer 42 output signals with scan position signals in order to provide a visible display of the distribution of one or more chemical elements on the screen 51 of a cathode ray tube display device 52.

The display device 52 of this example is a cathode ray tube display in order to provide a high degree of image definition. An oscilloscope may also be used or a television receiver set may be employed if the input signals from pulse height analyzer 42 and sweep frequency generators 26 and 27 are processed through a video scan converter.

As is understood in the art, a display device 52 of this type generates a point of visible light 53 which is swept in a raster pattern 54 of parallel scan lines in response to X and Y sweep frequency signals and which has an intensity which varies in accordance with the amplitude of an intensity signal. For the present purposes the X and Y sweep frequency signals from generators 26 and 27 respectively are applied to the X and Y raster control terminals 56 and 57 respectively of the display device 52 to synchronize the scanning motion of the point of light 53 with the scanning motion of the primary x-rays 13 at object 14.

The display device 52 of this embodiment is of the color type having three intensity signal terminals 58, 59 and 61 which respectively control the red, green and blue components of the point of light 53. Output channels 44, 46 and 47 of the pulse height analyzer 42 are coupled to intensity signal terminals 61, 59 and 58 respectively through separate ones of a series of amplifiers 62. Thus the intensity of a particular one of the colors, such as blue for example, is modulated in the course of the scanning operation by changes in the rate of detection of fluorescent x-rays that identify a specific element. The relative intensity of blue at different portions of the visible image then corresponds to the distribution of that element within the scanned region of the object 14. Similarly, green and red in the visible image depict the distribution of two additional elements.

It is advantageous if the amplifiers 62 are of the type having adjustable time constants as this provides for optimum adjustment to different average rates of detection of fluorescent x-rays 37. In operations where the detection rate is sufficiently low that detector 38 produces discrete output pulses in response to individual x-rays, the time constants maY be shortened to cause distinct dots to be produced at screen 51 in response to such individual x-rays. Variations in the amount of an element at different regions of the object 14 are then represented by variations of dot density between corresponding regions of the image on screen 51. In other operations where fluorescent x-rays 37 are produced and detected at a higher rate which prevents individual processing of each x-ray count, amplifiers 62 are adjusted to have longer time constants so that the amplitudes of the intensity signals applied to display terminals 58, 59 and 61 vary in proportion to variations in the level of detection of fluorescent x-rays. In this mode of operation, variations in the amount of an element between different regions of the object 14 are represented by brightness variations between corresponding regions of the image at screen 51.

If the distribution of only a single element is of interest, pulse height analyzer 42 may have only a single output channel coupled to a single intensity signal terminal of the display device 52. Thus a monochromatic or black and white display device may be used in such cases. It is also possible to represent the distribution of more than three elements simultaneously. For example, as depicted in FIG. 1, the fourth pulse height analyzer output channel 48 receives count signaLs indicative of a fourth element. A pair of additional amplifiers 63 coupled channel 48 to both the red and green intensity signal terminals 58 and 59 respectively. Thus the spatial distribution of the fourth element is represented in yellow in the image. Additional combinations of the primary colors red, green and blue may be used to represent still additional elements.

If the element distribution data is to be obtained with only a single raster scan or a small number of raster scans, the display device 52 may be of the form having a variable persistence control 64 which provides for retaining an image on the screen 51 for a selected time after the image has been initially generated.

A permanent record of the results of a scanning operation may be made by photographing the display at screen 51. The signals from sweep frequency generators 26 and 27 together with the output signals from pulse height analyzer 42 may also be recorded at a disc storage, magnetic tape or the like for subsequent playback to the display device 52 or for analysis by data processing techniques. Such signals may also be subjected to various image enhancement procedures known to the art.

The regions between the scanning x-ray source 12, object 14 and detector 38 are enclosed by radiation absorptive shielding 66 for the protection of operator personnel and also to prevent ambient radiations from external sources from affecting the desired data. While the system does not inherently require that there be a vacuum in such regions there are some usages in which it may be preferable to evacuate the space between the x-ray source 12, object 14 and detector 38 to reduce absorption of very low energy x-rays or for other reasons. In such cases, the shielding structure 66 may also be designed to serve as a vacuum enclosure.

Advantageous variations of the above described apparatus may be made to adapt the system for specialized usages. FIG. 3, for example, depicts a second embodiment 11a particularly suited for checking uniformity of the thickness of a layer 67 of one material which is against a base or substrate 68 of different composition.

Amoung other usages, the layer thickness checking system 11a of FIG. 3 may be employed in the microsemiconductor industry for quality control purposes in the manufacture of semiconductor wafers 14a. Such wafers 14a may have a thin layer 67 of metallic electrical conductor, such as aluminum for example, which has been deposited on a thicker base layer 68 which may typically be predominately formed of silicon. Microcircuit elements are fabricated by etching away portions of the metallic layer 67 while leaving the other portions to define electrically conductive paths of the microcircuit element. Defective microcircuit elements may be produced if the thickness of the metallic layer 67 is not uniform prior to the etching process. If an area of the layer 67 is too thick the etching operation may not fully penetrate through portions of the layer that are intended to be removed. The microcircuit element may then exhibit short circuits. Conversely, areas of the layer 67 which are too thin may be etched away to a greater extent than was intended leaving open circuits where conductive paths are meant to be present. The apparatus of FIG. 3 provides for detection of wafers 14a which have a non-uniform layer 67, prior to etching, so that wafers which might result in a defective microcircuit element can be eliminated from costly further processing.

For clarity of illustration the wafer 14a including metallic layer 67 and substrate layer 68 are depicted in FIG. 3 with a substantially greater thickness than is typically the case in practice.

The scanning x-ray spectrometer 11a of FIG. 3 may be similar in many respects to the previously described embodiment. The scanning x-ray source 12a again has a vacuum envelope 17a with an electron gun 18a at one end which directs an electron beam 19a to a target plate 21a at the opposite end. Beam deflection means 23a including a magnetic deflection yoke 24a controlled by X and Y sweep frequency generators 26a and 27a respectively sweep the electron beam 19a in a raster pattern of parallel scan lines at the target plate 21a to generate a moving primary x-ray origin point 33a. A collimator 28a, transpierced by an array of radiation transmissive passages 31a, causes the primary x-rays 13a to scan along the wafer 14a in a similar raster pattern in the manner previously described. Fluorescent x-rays 37a originating at the moving irradiated area 34a are detected by a shielded, liquid nitrogen cooled solid state detector 38a having a preamplifier 41a which produces count signals having amplitudes indicative of the energies of the detected x-rays.

Collimator 28a differs from that of the previously described embodiment in that it is inverted so that the radiation transmissive passages 31a are divergent in the direction of the scanned object 14a. Thus the scan raster at object 14a is larger than the electron beam 19a scan raster at target plate 21a. While this decreases resolution, it is also advantageous under certain circumstances. In particular the target plate 21a may be of smaller diameter than would otherwise be necessary and therefore may also be relatively thin while retaining sufficient structural strength to withstand the pressure caused by the presence of vacuum at one side of the plate. A thin target plate 21a is advantageous when soft or low energy primary x-rays 13a are being utilized since less absorption of such x-rays occurs in a thinner plate. As will hereinafter be discussed in more detail, low energy primary x-rays 13a are relied upon for detecting the thickness of an aluminum layer 67 on a silicon substrate 68.

As significant absorption of such low energy primary x-rays may occur in passage through air, the enclosure 66a around the target plate 21a, scanned object 14a and detector 38a in this embodiment is a vacuum enclosure as well as providing for radiation shielding so that the enclosed region may be evacuated during scanning operations.

More accurate output data may be obtained by disposing a second multi-apertured collimator 28b between the scanned object 14a and detector 38a. The second collimator 28b may be of the same general type as the previously described collimator 28a and thus has spaced apart radiation transmissive zones 31b each directed between detector 38a and a separate point along the scan path at object 14a. The second collimator 28b suppresses scattered x-rays from the region of object 14a that might otherwise cause erroneous counts at detector 38a.

In some usages the scanning x-ray spectrometer 11a may be employed to monitor the thickness of wafer 14a layers or the like while the wafers are being carried on a moving conveyer belt or are otherwise being traveled. In such instances it is preferable that the x-ray source 12a be adjusted to scan lines on the wafers 14a which are transverse to the direction of motion of the wafers.

A raster pattern 54a corresponding to the primary x-ray 13a scanning pattern at wafer 14a is established at the screen 51a of a cathode ray tube display device 52a by coupling X and Y sweep frequency generators 26a and 26a to the X and Y raster control terminals 56a and 57a respectively of the display device. As it is necessary, at any given time, to display variations of only a single chemical element in the scanned region of wafer 14a the display device 52a of this embodiment may be of the monochromatic or black and white type having only a single intensity signal terminal 69.

For similar reasons the means 71 for identifying detected fluorescent x-rays 37a characteristic of the element being detected may have only a single output channel 72 coupled to the intensity signal terminal 69. Means 71 further includes an amplifier 43a which transmits shaped pulses from detector preamplifier 41a to a single channel analyzer 42a of the known form which transmits only pulses having a predetermined range of amplitudes, the amplitudes in the present case being those which identify the chemical element of the substrate layer 68 of wafer 14a. An additional amplifier 62a transmits such pulses from analyzer 42a to intensity signal terminal 69 through a switch 73 when the switch is in the closed position.

Thus, in operation, the intensity of successive points in the visible image displayed at screen 51a varies in accordance with variations in the rate of detection of fluorescent x-rays of the element of substrate layer 68 at corresponding points in the scanned region of wafer 14a. Absorption of such fluorescent x-rays in passage from substrate layer 68 to detector 38a varies in accordance with variations in the thickness of the upper layer 67 at successive points along the scan. Thus the image at screen 51a exhibits variations in brightness which correspond to variations of the thickness of the upper layer 67.

If the fluorescent x-rays of the substrate layer 68 element are too weakly absorbed or too strongly absorbed in the upper layer 67 because of absorption edge considerations or because of the thickness of the upper layer, more accurate results may be obtainable by directly determining the thickness of the upper layer by detecting and identifying fluorescent x-rays from an element in the upper layer itself. For this purpose, means 71 of this embodiment includes a second single channel analyzer 42b, output amplifier 62b and switch 74 connected between amplifier 43a and intensity signal terminal 69 in parallel with analyzer 42a, amplifier 62a and switch 73. Analyzer 42b transmits only pulses having amplitudes which identify fluorescent x-rays 37a characteristic of an element found in upper layer 67 but not found in the substrate layer 68. Thus the display at screen 51a is again indicative of variations of the thickness of the upper layer 67 although the image is a reversal or negative of that obtained by utilizing the first analyzer 42a.

In some circumstances it may be highly useful to produce both a positive image and a reversal image by first utilizing analyzer 42a and than utilizing analyzer 42b. Techniques for enhancing gray level variations in a cathode ray tube display are known in which the two sets of intensity signals are digitized and ratios are obtained on a point by point basis by computer analysis. The ratios are then converted to analog signals which are fed back to the display device as enhanced intensity signals.

Use of analyzer 42a in particular may be preferable for checking typical semiconductor wafers 14a having a thin layer of aluminum 67 and a silicon substrate 68. The characteristic fluorescent x-rays 37a of silicon have energies of about 1.8 kev and are therefore absorbed very little in silicon itself as that is less energy than is needed to produce K electrons in silicon. However, it is sufficient energy to allow such x-rays to be easily absorbed by a thin layer of aluminum as it is close to but somehwat higher than the energy of the K absorption edge of aluminum which is 1.56 kev. Thus the proportion of the fluorescent x-rays 37a from silicon substrate 68 that is transmitted through the aluminum layer 67 depends strongly on the thickness of the aluminum layer near the x-ray origin point 34a.

More accurate results are obtained if the origin point 34a of the silicon fluorescent x-rays is at or close to the aluminum-silicon boundary. The high voltage applied to electron gun 18a by high voltage supply 20a may be adjusted to provide low energy primary x-rays 13a that will not penetrate too far into the silicon substrate 68, the primary x-ray energy for this purpose preferably being higher than the K absorption edge energy of silicon by an amount just sufficient to avoid significant image degradation from scattering effects. If the energy of the primary x-rays 13a is too close to the silicon K absorption edge, x-rays scattered from the aluminum layer 67 may interfere with detection of the silicon fluorescent x-rays and cause undesirable background noise in the image at screen 51a. Control of the primary x-ray energy in this manner may not be significant if the silicon layer 68 itself is very thin.

In this particular example, a very large proportion of the x-ray fluorescence in wafer 14a originates in the silicon substrate 68 because of the relative thinness of the aluminum layer 67 but most of the silicon x-ray fluorescence absorption occurs in the aluminum layer because of the energy and absorption edge factors discussed above. Thus the rate of detection of silicon fluorescent x-rays 37a detector 38a varies exponentially with the thickness of the aluminum layer along the scan path.

Still another mode of operation may be realized by inverting the wafer 14a so that the silicon substrate layer 68 faces the scanning x-ray source 12a. The silicon substrate layer 68 then acts as a primary x-ray filter in front of the aluminum layer 67. Primary x-rays 13a having energies above the K absorption edge energy of silicon tend to be absorbed in the silicon layer 68 while lower energy primary x-rays are transmitted to the aluminum layer 67 to produce the desired x-ray fluorescence.

The above described examples of analysis techniques which may be accomplished with the apparatus of FIG. 3 include detecting variations in the absorption of fluorescent x-rays from the substrate layer 68 in the layer 67 of interest and detecting variations of fluorescent x-ray emission by the layer 67 of interest itself either directly or after passage of such x-ray emission through the substrate layer 68, the choice of techniques to be used in a particular case being dependent on such factors as the compositions and thicknesses of the layers. Other procedures are possible and it should also be recognized that the apparatus may be used for thickness analysis of objects other than the described wafers 14a that have a layer 67 of aluminum on a silicon substrate layer 68. Similarly procedures may be used for the analysis of other types of layered structure of which nickel on chromium, phosphorus on silicon oxide and titanium on tungsten are some additional examples.

While the invention has been described with respect to certain preferred embodiments, many modifications are possible and it is not intended to limit the invention except as defined in the following claims.

I claim:

1. In an x-ray spectrometer for detecting the distribution of at least one chemical element within an object and having scanning means for directing primary x-rays to successive points situated along a scan path on said object, detector means for detecting fluorescent x-rays emitted from said object in response to said primary x-rays, and means for detecting variations of the amount of said element along said scan path by analyzing the energy of said fluorescent x-rays the improvement comprising:

said scanning means having a charged particle beam source, a target plate formed of material which produces x-rays in response to said charged particle beam, and beam deflector means for establishing a varying electrical and/or magnetic field in the path of said charged particle beam to sweep said charged particle beam along an impact path on said plate which corresponds to said scan path on said object, and means for suppressing detection of said primary x-rays by said detector means.

2. The apparatus of claim 1 wherein said means for suppressing detection of said primary x-rays includes a collimator situated between said target plate and said scan path, said collimator having a volume of x-ray absorbent material transpierced by a plurality of radiation transmissive zones which are directed at said successive points along said scan path and directed away from said detector means.

3. The apparatus of claim 1 wherein said beam deflector means sweeps said charged particle beam along a plurality of substantially parallel impact paths on said target plate, further including collimator means for directing primary x-rays originating at each of said impact paths away from said detector means and towards a corresponding one of a plurality of substantially parallel scan paths on said object.

4. The apparatus of claim 1 wherein said means for detecting variations produces separate output signals on each of a plurality of separate output signal channels, signals on each of said output signal channels being indicative of variations of the amount of a different single one of a plurality of chemical elements along said scan path on said object, further including:

means for generating scan position signals that identify said successive points along said scan path, and a cathode ray tube having means for generating visible data displays by sweeping a visible light origin point along at least one scan line on a screen in response to said scan position signals, means for modulating the intensity of said visible light at said origin point in response to said output signals, and means for producing a different color of visible light at said origin point in response to output signals received from each separate one of said output signal channels.

5. The apparatus of claim 1 further including a collimator disposed between said target plate of said scanning means and said scan path on said object and having a plurality of radiation transmissive zones extending between said successive points along said scan path of said object and corresponding succesive points along said impact path of said target plate, wherein said radiation transmissive zones are convergent in the direction of said scan path and directed away from said detector means.

6. In an x-ray spectrometer for detecting the distribution of at least one chemical element within an object and having scanning means for directing primary x-rays to successive points situated along a scan path on said object and means for detecting variations of the amount of said element along said scan path by analyzing the energy of fluorescent x-rays emitted from said object in response to said primary x-rays, the improvement comprising:

said scanning means having a charge particle beam source, a target plate formed of material which produces x-rays in response to said charged particle beam, and beam deflector means for sweeping said charged particle beam along an impact path on said plate which corresponds to said scan path on said object, further including a collimator disposed between said target plate of said scanning means and said scan path on said object and having a plurality of radiation transmissive zones extending between said successive points along said scan path of said object and corresponding successive points along said impact path of said target plate, wherein said radiation transmissive zones are divergent in the direction of said scan path.

7. A scanning x-ray spectrometer for determining the distribution of at least one chemical element within a predetermined region comprising:

a target plate formed at least in part of material which emits primary x-rays when high energy electrons impact thereon, electron gun means for directing an electron beam to said target plate, beam deflector means for establishing a varying electrical and/or magnetic field between said target plate and said electron gun means for deflecting said electron beam through a predetermined raster pattern to provide a moving primary x-ray origin point at said plate, a collimator disposed between said target plate and said region and having radiation transmissive zones alternated with radiation absorbent zones, said radiation transmissive zones being aligned to direct primary x-rays from points on said raster pattern at said target plate to corresponding points along a scan path in said region, means for detecting fluorescent x-rays which are emitted from said corresponding points along said scan path in response to said primary x-rays, said detection means being situated away from the paths of said primary x-rays, means for identifying detected fluorescent x-rays which have energies corresponding to those of the characteristic x-rays of said chemical element, and means for indicating variations in the rate of detection of said fluorescent x-rays which have energies corresponding to those of the characteristic x-rays of said chemical element.

8. In a method of determining the spatial distribution of at least one chemical element within a subject, wherein primary x-rays are directed to a scan path at said subject, and wherein the relative amounts of said chemical element at locations along said scan path are determined by analyzing the energies of fluorescent x-rays emitted from said locations in response to said primary x-rays, the improvement comprising:

generating a moving origin point of said primary x-rays by directing a charged particle beam to a relatively broad target and deflecting said charge particle beam by establishing an electrical and/or magnetic field in the path thereof including varying said field to travel the impact point of said beam on said target along an impact path thereon which corresponds to said scan path at said subject, blocking said primary x-rays from a predetermined region, and detecting said fluorescent x-rays at said predetermined region.

9. The method of claim 8 including the further steps of sequentially transmitting said primary x-rays from said moving origin point to each of said locations along said scan path while blocking said primary x-rays from others of said locations.

10. In a method of detecting the spatial distribution of chemical elements in a region, the steps comprising:

directing an electron beam through an electrical and/or magnetic field to a relatively broad target to produce primary x-rays by impact of said electron beam on said target, generating scan position signals which define a raster pattern, varying said field in accordance with said scan position signals to deflect said electron beam relative to said target to provide a moving x-ray origin point thereat which follows said raster pattern, directing primary x-rays which originate at successive positions in said raster pattern at said target to corresponding successive locations in said region while blocking said primary x-rays from others of said successive locations therein, detecting the energies of fluorescent x-rays which are emitted from said successive locations in response to said primary x-rays and which travel to a detector location, blocking said primary x-rays from said detector location, analyzing said detecting x-ray energies to identify characteristic fluorescent x-rays of said chemical elements, and correlating said identified characteristic fluorescent x-rays with said scan position signals to indicate said spatial distribution of said chemical elements in said region.

* * * * *